United States Patent
Isobe

(10) Patent No.: US 8,048,536 B2
(45) Date of Patent: Nov. 1, 2011

(54) SINGLE-LAYER ORGANIC EL DEVICE

(75) Inventor: Shinichiro Isobe, Fukuoka (JP)

(73) Assignee: Mitsubishi Heavy Industries Ltd., Tokyo (JP)

(*) Notice: Subject to any disclaimer, the term of this patent is extended or adjusted under 35 U.S.C. 154(b) by 752 days.

(21) Appl. No.: 10/584,313

(22) PCT Filed: Dec. 22, 2004

(86) PCT No.: PCT/JP2004/019211
§ 371 (c)(1),
(2), (4) Date: Aug. 11, 2006

(87) PCT Pub. No.: WO2005/061657
PCT Pub. Date: Jul. 7, 2005

(65) Prior Publication Data
US 2007/0116981 A1 May 24, 2007

(30) Foreign Application Priority Data
Dec. 24, 2003 (JP) .................. 2003-427275

(51) Int. Cl.
*H01L 51/54* (2006.01)
*C09K 11/06* (2006.01)
(52) U.S. Cl. .......... 428/690; 428/917; 313/504; 257/40; 257/E51
(58) Field of Classification Search ............. 428/690, 428/917, 411.1, 336; 313/502–509; 257/40, 257/88, 104, E51; 532/1
See application file for complete search history.

(56) References Cited

U.S. PATENT DOCUMENTS

| | | | | |
|---|---|---|---|---|
| 4,720,432 A | * | 1/1988 | VanSlyke et al. | 428/457 |
| 5,059,863 A | * | 10/1991 | Tashiro et al. | 313/504 |
| 6,103,446 A | | 8/2000 | Devlin et al. | |
| 6,114,463 A | | 9/2000 | Chen et al. | |
| 6,146,809 A | | 11/2000 | Devlin et al. | |
| 6,436,558 B1 | | 8/2002 | Sato et al. | |
| 2001/0004107 A1 | | 6/2001 | Hanna et al. | |
| 2001/0016269 A1 | | 8/2001 | Otani et al. | |
| 2003/0091862 A1 | | 5/2003 | Tokito et al. | |
| 2003/0165715 A1 | | 9/2003 | Yoon et al. | |
| 2004/0219387 A1 | * | 11/2004 | Li et al. | 428/690 |

FOREIGN PATENT DOCUMENTS
EP 1645552 4/2006
(Continued)

OTHER PUBLICATIONS
Hong, Y., Miller, L. L., Graf, D. D., Mann, K. R., Zinger, B. Synthetic Metals 82 (1996) 189-191.*
(Continued)

*Primary Examiner* — Angela Ortiz
*Assistant Examiner* — J. L. Yang
(74) *Attorney, Agent, or Firm* — Wenderoth, Lind & Ponack, L.L.P.

(57) ABSTRACT

Disclosed is an organic EL dye enabling to provide an organic EL device which is capable of emitting a light at a low voltage even when it has a single layer structure. Also disclosed is an organic EL device using such an organic EL dye. The organic EL dye is represented by the general formula (1): (Y—L) nXm wherein x is an n-valent charge-transporting group, Y is a light-emitting group, L is a linking group bonding the charge-transporting group and the light-emitting group, and m and n are respectively an integer not less than 1.

2 Claims, 3 Drawing Sheets

FOREIGN PATENT DOCUMENTS

| | | | | |
|---|---|---|---|---|
| JP | 02-210790 | | | 8/1990 |
| JP | 10-101738 | | | 4/1998 |
| JP | 11-144526 | | | 5/1999 |
| JP | 2000-282024 | | | 10/2000 |
| JP | 2000282024 | A | * | 10/2000 |
| JP | 2001-509832 | | | 7/2001 |
| JP | 2002-356489 | | | 12/2002 |
| JP | 2003-133072 | | | 5/2003 |
| JP | 2003-151778 | | | 5/2003 |
| JP | 2003-157977 | | | 5/2003 |
| JP | 2003133072 | A | * | 5/2003 |
| JP | 2003151778 | A | * | 5/2003 |
| JP | 2003157977 | A | * | 5/2003 |
| JP | 2003-217856 | | | 7/2003 |
| JP | 2003217856 | A | * | 7/2003 |
| JP | 2003-342325 | | | 12/2003 |
| JP | 2004-224774 | | | 8/2004 |
| WO | 02/088274 | | | 11/2002 |

OTHER PUBLICATIONS

Machine English translations of the following foreign patent documents: JP2000282024A, JP2003133072A, JP2003151778A, JP2003217856A, and JP2003157977.*

Ishii H.; Sugiyama, K.; Yoshimura D.; Ito, E.; Ouchi, Y.; Seki, K. IEEE Journal of Selected Topics in Quantum Electronics, vol. 4, No. 1, Jan./Feb. 1998.*

Supplementary European Search Report issued Dec. 23, 2008 in the International (PCT) Application of which the present application is the U.S. National Stage.

C. W. Tang, S.A. Vanslyke, Appl. Phys. Lett., 51, (12), Sep. 21, 1987, 913-915.

Chinese Office Action issued Aug. 28, 2009 in connection with corresponding Chinese Application No. 200480038650.X (with English translation).

European Office Action issued Sep. 10, 2009 in connection with corresponding European Application No. 04 807 568.3, in the English language.

Y. Hong et al. "Electroluminescence from a polyester containing oligothiophenes in the main chain, enhanced by a diimide electron transport agent", Synthetic Metals, vol. 82, pp. 189-191 (1996).

Notification of Reasons for Refusal issued Mar. 8, 2010 in corresponding Japanese Application No. 2005-516509, with English translation.

Canadian Office Action issued Aug. 30, 2010 in corresponding Canadian Application No. 2,551,723, in the English language.

* cited by examiner a.

b.

c.

d.

SINGLE-LAYER ORGANIC EL DEVICE

TECHNICAL FIELD

The present invention relates to a single-layer organic EL device.

BACKGROUND ART

Currently, in the field of electronics devices, research and development of an organic electroluminescence (EL) dye have been intensively done aiming for a next-generation light-emitting material taking the place of a liquid crystal. Theoretically, the organic EL dye can emit light with small electric power, because the dye molecule itself can emit light by feeding a current through a thin film comprising a molecular assembly of the dye. Thus, researches for application to a monitor for electro devices and commercialization are pursued at a high pace aimed at taking the place of a liquid crystal display of high power consumption.

As for the structure of the organic EL device, an organic hole transport layer and an organic electron transport layer are retained between an anode and a cathode, and an organic luminescent dye is contained in the organic hole transport layer and/or the organic electron transport layer, and upon injecting an electron from electrodes into the organic hole transport layer and the organic electron transport layer, respectively, a hole and an electron being combined, and light is emitted when the dye is relaxed from an excited state to a ground state. Therefore, by forming a panel having a multi-layer structure in which a function of carrier-mediated transport and a function of light emission are separated, for example, a two-layer structure of a hole transport layer including a hole-transporting material and an emission layer described in, for example, C. W. Tang, S. A. VanSlyke, Appl. Phys. Lett., 51, (12), 21, Sep. 1987, 913-915, or a three-layer structure in which an electron transport layer including an electron-transporting material is added to the above two-layer structure, the efficiency of recombination of the hole and the electron is enhanced and light is emitted at a low voltage of the order of 10 V. However, in the case of such an organic EL device, since light is predominantly emitted at an interface between the hole transport layer and the emission layer, which is an electron transport layer, by its function as shown in FIG. 6, there is a problem that sufficient emission efficiency can not obtained.

Further, when a multi-layer structure is employed as a device structure, it is necessary to precisely control a film thickness in a plurality of film formation steps and form a pinhole-free film, and therefore there is a problem that time and cost required for producing a device increase.

For this problem, a device structure having a single-layer structure can provide a possibility that the device can be manufactured at a lower cost. Therefore, as a device of a single-layer structure, for example, an organic EL device using an organic compound having both of a hole-transporting ability and an electron-transporting ability is proposed in Japanese Laid-Open Patent Publication No. 2-210790, but a driving voltage is as high as 20 V and emission brightness is not enough.

DISCLOSURE OF INVENTION

The present invention has been made in order to resolve the above problems, and it is an object of the present invention to provide an organic EL device which is capable of emitting light at a low voltage even when it has a single-layer structure.

The present inventors made earnest investigations concerning the thin film structures of conventional single-layer organic EL devices, and consequently have found that just only bonding organic compounds having both of a hole-transporting ability and an electron-transporting ability, respectively, to each other is not enough, and by holding an organic compound having a charge-transporting ability as a core between organic compounds having a light-emitting ability as illustrated in FIG. 5, a hole and an electron are distributed throughout the thin film and sufficient emission brightness can be attained at a low driving voltage.

That is, the organic EL dye of the present invention is a compound represented by the general formula: $(Y-L)nXm$ (1), wherein X is a n-valent charge-transporting group, Y is a light-emitting group, L is a linking group bonding the charge-transporting group and the light-emitting group, and m and n are respectively an integer not less than 1.

As for a combination of the above m and n, when m and n are 1, respectively, $(Y-L)nXm$ becomes $Y_1-L-X$.

When m is 1 and n is 2, it is possible to produce not only $Y_1-L-X-L-Y_1$, but also
$Y_1-L-X-L-Y_2$,
$Y_1-L_1-X-L_2-Y_1$ and
$Y_1-L_1-X-L_2-Y_2$.
$(Y_1-L)_3-X$, in which m is 1 and n is 3, can also be produced.

In addition, when n=m, the above general formula can be represented by $(Y-L-X)n$, and it is possible to produce
$Y_1-L-X-L-Y_1-L-X-L-Y_1$, and
$Y_1-L-X_1-L-Y_1-L-X_2-L-Y_1$.

Further, in the above production example, the organic EL device is formed so as to hold the charge-transporting group as a core between the light-emitting groups, but the organic EL device may be formed so as to hold the light-emitting group as a core between the charge-transporting groups, that is, so as to hold the light-emitting group as a core between hole-transporting group and electron-transporting group, or between the hole-transporting group and the electron-transporting group.

The reason why the organic EL dye of the present invention emits light at a low voltage is not clear, but it is conceivable as the reason for such light emission that by virtue of the presence of the charge-transporting group, the conductivity of the emission layer is enhanced and holes or electrons gather around the charge-transporting group and therefore the efficiency of recombination of the hole and the electron is enhanced.

Thus, by forming the emission layer 4 on a substrate 1 interposing an anode 2 and providing a cathode 3 thereon, as shown in FIG. 1, without forming a multi-layer structure, it becomes possible to emit light at a low voltage even in a single-layer structure containing the organic EL dye. However, a hole injection layer 5 (FIG. 2) or an electron injection layer 6 (FIG. 3), or both injection layers 5 and 6 (FIG. 4) may be further provided as required.

Further, when the above-mentioned X is a hole-transporting group, a monocyclic or polycyclic aromatic group can be used for this hole-transporting group. Any one species selected from the group consisting of an anthracene group, a phenanthrene group, a pyrene group, a fluorene group and a biphenylene group can be used for this hole-transporting group. Further, a hole-transporting group having a tertiary amine group can also be used.

Further, when the above-mentioned Y is an electron-transporting group, a monocyclic or polycyclic aromatic group containing a heteroatom can be used for this electron-transporting group. Further, a naphthalenediimide group or a phenyldiimide group can be used for this electron-transporting group.

The organic EL dye, which has an acceptor such as naphthalenediimide as a core, gathers electrons and has a tendency to decrease in efficiency if the dye has a heterocyclic skeleton. In this case, the dye formed by bonding a hole-transporting site such as diphenylamine to a dye structure has high efficiency and gathers holes and electrons.

Formula 1

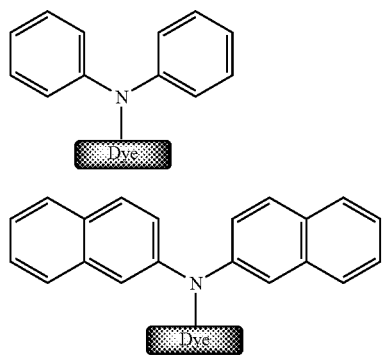

Formula 2

By using a dye having such a structure, a compound, which has naphthalenediimide as a core, can gather holes and electrons around a molecule with efficiency and can also improve emission efficiency.

Formula 3

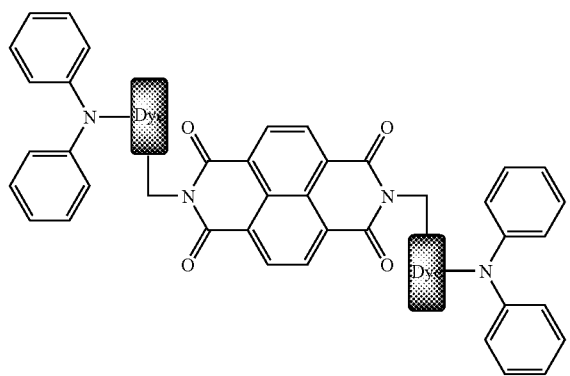

Further, a compound of the general formula $A_1—R_1—A_2$ (2) can be used for the above-mentioned L. Here, $A_1$ is a first bonding group to be bonded to the above charge-transporting group, $A_2$ is a second bonding group to be bonded to the above light-emitting group, and $R_1$ is a spacer group linking the first bonding group with the second bonding group.

Further, an alkylene group or an alkylene group having a heteroatom on a main chain can be used for the above-mentioned $R_1$.

Further, a heteroatom can be used for the above-mentioned $A_1$. Further, any one species selected from the group consisting of a substituted or unsubstituted alkyl group, an ether group, a thioether group, a substituted or unsubstituted imino group, an amide group and an ester group can be used for the above-mentioned $A_2$.

Further, an organic EL device of the present invention is characterized by that the device has an organic layer of a single-layer formed by sandwiching the organic layer between a pair of electrodes and this organic layer contains the organic EL dye represented by the above-mentioned general formula (1).

By employing the organic EL dye of the present invention in the emission layer, it becomes possible to provide an organic EL device emitting light at a low voltage equivalent to or at a lower voltage than that in a device of a multi-layer structure even when it has a single-layer structure. Thereby, it becomes possible to simplify a production process more and prepare an organic EL dye of a lower cost.

BEST MODE FOR CARRYING OUT THE INVENTION

Figure 1:
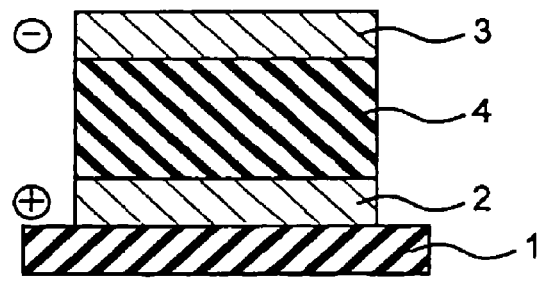
FIG. 1 is a conceptual view of a single-layer organic EL device in accordance with the present invention.
Figure 2:
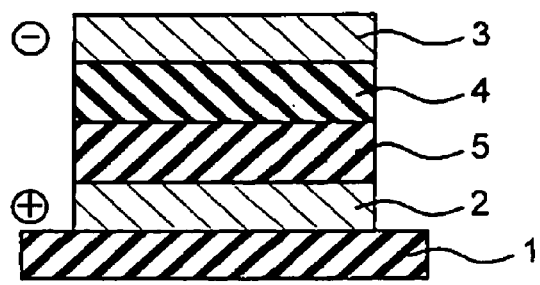
FIG. 2 is a conceptual view of a structure in which a hole injection layer is provided on a positive side of an emission layer of the single-layer organic EL device in accordance with the present invention.
Figure 3:
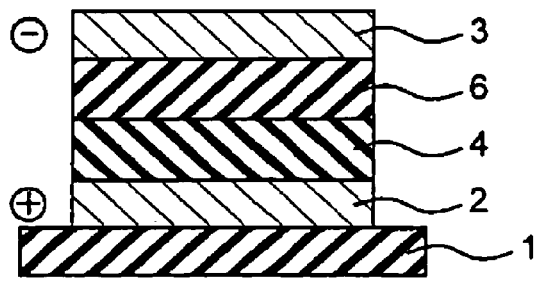
FIG. 3 is a conceptual view of a structure in which an electron injection layer is provided on a negative side of an emission layer of the single-layer organic EL device in accordance with the present invention.
Figure 4:
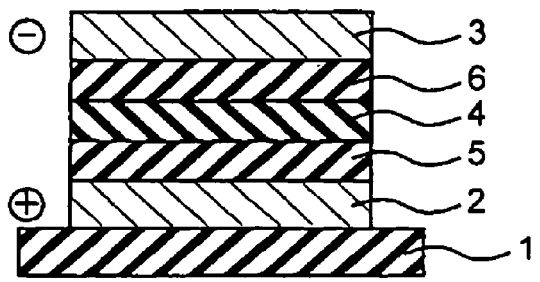
FIG. 4 is a conceptual view of a structure in which a hole injection layer is provided on a positive side and an electron injection layer is provided on a negative side of an emission layer of the single-layer organic EL device in accordance with the present invention.
Figure 5:
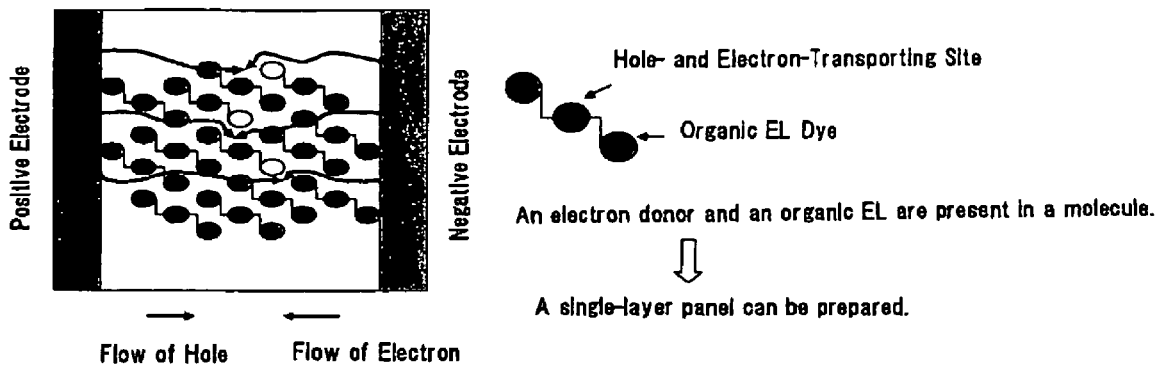
FIG. 5 is a view illustrating a function of the single-layer organic EL device of the present invention.
Figure 6:
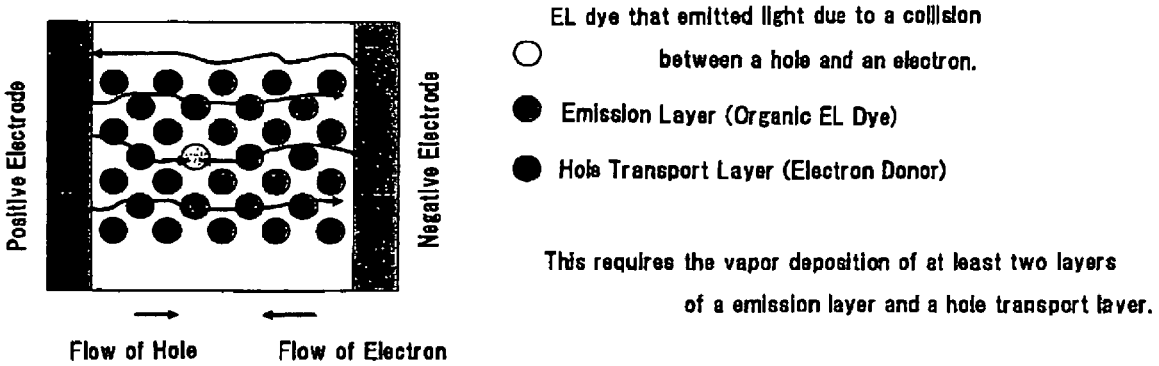
FIG. 6 is a view illustrating a function of a conventional organic EL device.

Hereinafter, the embodiment of the present invention will be described in detail.

A particularly preferred organic EL dye of the present invention is a compound represented by the general formula (Y—L)nX (1), wherein X is an n-valent charge-transporting group, Y is a light-emitting group, L is a linking group bonding the charge-transporting group and the light-emitting group, and n is an integer not less than 1.

The charge-transporting group is required to enhance the efficiency of injecting a charge from an electrode and to have high charge mobility for transferring the injected charge with efficiency.

When a hole-transporting group is used for the charge-transporting group, a monocyclic or polycyclic aromatic group can be used for the hole-transporting group. Preferably, the polycyclic aromatic group, more preferably a condensed aromatic group having a planar property and a higher electron-donating property can be used. As a specific example, any one species selected from the group consisting of an anthracene group, a phenanthrene group, a pyrene group, a fluorene group and a biphenylene group, more preferably an anthracene group, a phenanthrene group or a pyrene group, can be used for the hole-transporting group.

In addition, number (n) of valences of the hole-transporting group is preferably 1 to 4 and more preferably 2.

Further, a substance having a tertiary amine group (—N(Ar$_1$)(Ar$_2$)) can also be used for the hole-transporting group. The reason for this is that a hole-transporting property (hole mobility) is enhanced since the tertiary amine group has an electron-donating property. Here, Ar$_1$ and Ar$_2$ are independent of each other and they are a substituted or unsubstituted monocyclic or polycyclic aromatic group.

As for the specific constitution of the hole-transporting group having the tertiary amine group, for example, number (n) of valences of the hole-transporting group is at least 2, and one of substitution sites is a tertiary amine group and the other substitution sites are bonded to a light-emitting group through a linking group. Alternatively, one of substitution sites is a tertiary amine group to which the hole-transporting group is bonded through the linking group and the other substitution sites are bonded to a light-emitting group through a linking group.

When an electron-transporting group is used for the charge-transporting group, a monocyclic or polycyclic aromatic group containing a heteroatom can be used for the electron-transporting group. Preferably, the polycyclic aromatic group containing a heteroatom, more preferably a condensed aromatic group having a heteroatom and a planar property and a higher electron-accepting property can be used. As a specific example, a naphthalenediimide group or a phenyidiimide group, more preferably the naphthalenediimide group can be used. In addition, the naphthalenediimide group includes 1,8,4,5-naphthalenediimide and 2,3,6,7-naphthalenediimide.

In addition, number (n) of valences of the electron-transporting group is preferably 1 to 4 and more preferably 2.

A compound represented by the general formula A$_1$—R$_1$—A$_2$ (2) can be used for the linking group. Here, A$_1$ is a first bonding group to be bonded to the above charge-transporting group, A$_2$ is a second bonding group to be bonded to the above light-emitting group, and R$_1$ is a spacer group linking the first bonding group with the second bonding group.

As a specific example, an alkylene group or an alkylene group containing a heteroatom on a main chain is preferably used for the spacer group. A methylene group, an ethylene group or a trimethylene group is preferably used for the alkylene group. In addition, as an alkylene group containing a heteroatom on a main chain, an ethylene oxide group is preferably used and number of repeat is preferably 1 to 2. In addition to these, groups having an unsaturated bond such as alkene and alkyne may be used for the spacer group, and when these groups are used, there is a high effect of preventing stacking of a terminal dye and the charge-transporting group. Further, it is also possible to fix the charge-transporting group and the terminal dye in one plane by bonding an unsaturated group such as alkene or alkyne directly to the charge-transporting group.

Further, a heteroatom, preferably an oxygen atom or a nitrogen atom, can be used for the first bonding group. In addition, any one species selected from the group consisting of a substituted or unsubstituted alkyl group, ether group, thioether group, a substituted or unsubstituted imino group, amide group and ester group can be preferably used for the second bonding group.

Here, a role of the linking group is described.

The linking group secures linkage of the light-emitting group and the charge-transporting group through the first bonding group and the second bonding group. Further, while the presence of the spacer group secures a physical distance between the light-emitting group and the charge-transporting group to keep the flexibility in the choice of a molecular skeleton of the light-emitting group and the charge-transporting group, it inhibits stacking of the light-emitting group and the charge-transporting group to prevent a change in an emission wavelength or a reduction in emission intensity of the light-emitting group. Further, when a heteroatom is used for the first bonding group, there is an effect of inhibiting the conjugation or the electron resonance between the charge-transporting group and the light-emitting group to prevent a change in an emission wavelength or a reduction in emission intensity of the light-emitting group.

Further, when a heteroatom is used for the first bonding group, stacking can be more inhibited since an entire molecule can become a more rigid structure. In addition, it is also possible to suppress a structural change due to heat generation during passing an electric current to improve heat resistance.

Polycyclic aromatic compounds such as tetraphenylbutadiene and perylene, cyclopentadiene derivatives, oxadiazole derivatives, coumarin derivatives, distyrylpyrazine derivatives, acridone derivatives, quinacridone derivatives, stilbene derivatives, oxadiazolopyridine derivatives, imidazole derivatives, oxa(thia)diazolopyridine derivatives, thiadiazole derivatives, and tetraphenylthiophene derivatives can be used for the light-emitting group.

Specific examples of the above light-emitting groups can include, as polycyclic aromatic compounds, rubrene, anthracene, tetracene, pyrene, perylene, chrysene, decacyclene, coronene, tetraphenylbutadiene, tetraphenylcyclobutadiene, and pentaphenylcyclobutadiene.

Examples of cyclopentadiene derivatives can include 1,2,3,4-tetraphenyl-1,3-cyclopentadiene and 1,2,3,4,5-pentaphenyl-1,3-cyclopentadiene.

Examples of oxadiazole derivatives can include 2-(4'-t-butylphenyl)-5-(4'-biphenyl)1,3,4-oxadiazole and 2,5-bis(4-diethylaminophenyl)1,3,4-oxadiazole.

Examples of coumarin derivatives can include coumarin 1, coumarin 6, coumarin 7, and coumarin 30.

Examples of distyrylpyrazine derivatives can include 2,5-bis-(2-(4-biphenyl)ethenyl)pyrazine, 2,5-bis-(4-ethylsteryl)pyrazine, and 2,9-bis-(4-methoxysteryl)pyrazine.

Examples of acridone derivatives can include acridone and derivatives thereof.

Examples of quinacridone derivatives can include quinacridone and derivatives thereof.

Examples of stilbene derivatives can include 1,1,4,4-tetraphenyl-1,3-butadiene and 4,4'-bis(2,2-diphenylvinyl)biphenyl.

As oxadiazolopyridine derivatives, imidazole derivatives, oxa(thia)diazolopyridine derivatives, thiadiazole derivatives and tetraphenylthiophene derivatives, compounds represented by the general formulas in the specification can be used.

As for a preferred combination of the light-emitting group and the charge-transporting group, when the charge-transporting group is the hole-transporting group (electron-donating group), a preferred light-emitting group is a dye having an electron-accepting group. In addition, when the charge-transporting group is the electron-transporting group (electron-accepting group), a preferred light-emitting group is a dye having an electron-donating group. Number of the light-emitting groups linked with the charge-transporting group varies depending on a degree of a charge-transporting property of the charge-transporting group, but it is usually two or more molecules per one molecule of the charge-transporting group, and more preferably two molecules in order to keep a balance between the electron-donating property and the electron-accepting property.

When a compound having a donor property such as anthracene is used as a core, many combinations can be formed since most dyes are an acceptor. On the other hand, also in the case where an acceptor such as naphthalenediimide is used as a core, many combinations can be used since the dye gather electrons around a molecule. Particularly, when the compound having a donor property such as anthracene is used as a core, if the dye has a dye skeleton having a heterocyclic skeleton, this combination can be used. A dye having a halogen atom can also be used.

A preferred light-emitting group used in the present invention can include the following compounds.

1. Oxadiazolopyridine derivatives represented by the following general formula:

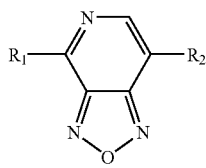

Formula 4 wherein $R_1$ and $R_2$ are independent from each other and represent an aromatic hydrocarbon group optionally having a substituent.

2. Imidazole derivatives represented by the following general formula:

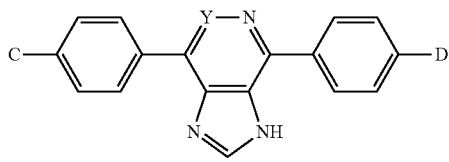

Formula 5 wherein C and D represent an aromatic hydrocarbon group optionally having another substituents including a carboxyl group or a heterocyclic group or an aromatic group containing a heteroatom in a ring, C and D may be identical with each other or different from each other, and Y represents a carbon atom optionally having a carboxyl group.

3. Oxa(thia)diazolopyridine derivatives represented by the following general formula:

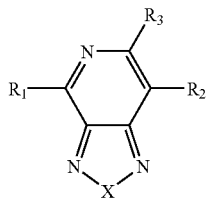

Formula 6 wherein $R_1$, $R_2$, $R_3$ and $R_4$ are independent from each another and represent an aromatic hydrocarbon group optionally having a substituent, X represents a nitrogen atom optionally having a substituent, a sulfur atom optionally having a substituent, an oxygen atom optionally having a substituent or a selenium atom optionally having a substituent, and $R_3$ represents a hydrogen atom, a cyano group, a carboxyl group, an amide group optionally having a substituent, an ester group optionally having a substituent, an alkyl group optionally having a substituent, an aromatic hydrocarbon group optionally having a substituent or a heterocyclic group optionally having a substituent.

4. Thiadiazole derivatives represented by the following general formula:

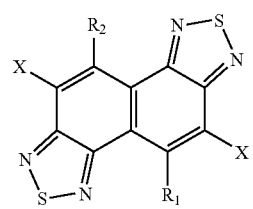

Formula 7 wherein $R_1$ and $R_2$ represent a hydrogen atom, a halogen atom, a cyano group, a nitro group, a carboxyl group, an alkyl group optionally having a substituent, an aralkyl group optionally having a substituent, an alkenyl group optionally having a substituent, an amino group optionally having a substituent, an amide group optionally having a substituent, an alkoxy group optionally having a substituent, an alkoxycarbonyl group optionally having a substituent, an alkoxysulfonyl group optionally having a substituent, an aromatic hydrocarbon group optionally having a substituent or a heterocyclic group optionally having a substituent, and X represents a hydrogen atom, a halogen atom, an alkoxy group or a hydroxyl group.

5. 2,3,4,5-tetraphenylthiophene derivatives 1 represented by the following general formula:

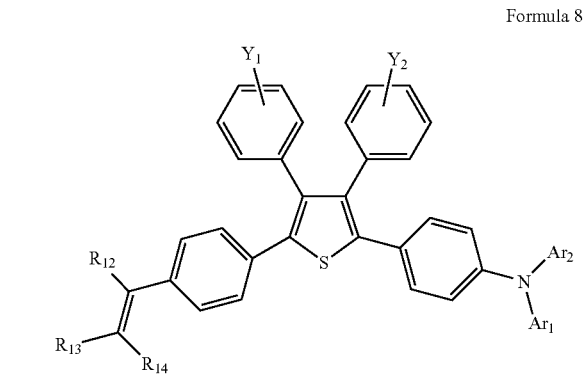

Formula 8 wherein groups of from $R_{12}$ to $R_{14}$ are independent from each another and represent a hydrogen atom, a straight chain, branched or cyclic alkyl group, a substituted or unsubstituted aryl group, or a substituted or unsubstituted aralkyl group, $Ar_1$ and $Ar_2$ represent a substituted or unsubstituted aryl group and further $Ar_1$ and $Ar_2$ may form a nitrogen-containing heterocycle together with a nitrogen atom to which they are bonded, and $Y_1$ and $Y_2$ represent a hydrogen atom, a halogen atom, a straight chain, branched or cyclic alkyl group, a straight chain, branched or cyclic alkoxy group, a substituted or unsubstituted aryl group, a substituted or unsubstituted aralkyl group, or a substituted or unsubstituted amino group.

6. 2,3,4,5-tetraphenylthiophene derivatives 2 represented by the following general frmula:

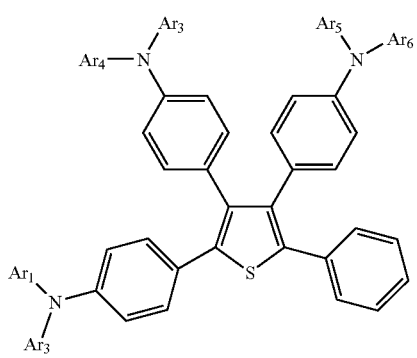

Formula 9 wherein groups of from $Ar_1$ to $Ar_6$ are independent of each another and represent a substituted or unsubstituted aryl group, and further $Ar_1$ and $Ar_2$, $Ar_3$ and $Ar_4$ and $Ar_5$ and $Ar_6$ may form a nitrogen-containing heterocycle together with a nitrogen atom to which they are bonded.

Hereinafter, the constitution of an organic EL device of the present invention will be described.

The organic EL device of the present invention has a constitution of a base 1, an anode 2, an emission layer 4 and a cathode 3 and an organic layer has a single-layer structure consisting of only the emission layer 4 as illustrated in FIG. 1.

The base plays a role of supporting a device and a transparent substrate can be used for the base. Glass or a transparent plastic sheet, for example, can be used for the transparent substrate.

An electrode material consisting of metal, alloy or conductive oxide, having a large work function (about 4 eV or more), can be used for the anode. As a specific example, gold, platinum, palladium, indium oxide, indium tin oxide (ITO) or tin oxide can be used. These electrode materials can be formed on a base by a vapor deposition method or a sputtering method. In addition, these electrode materials can also be used alone or in combination to form a multi-layer structure.

In addition, a thickness of the anode is 5 to 1000 nm and preferably 10 to 500 nm.

Metal having a small work function can be used for the cathode. For example, tin, magnesium, indium, calcium, aluminum, silver or alloys thereof can be used. These electrode materials can be formed by a vapor deposition method or a sputtering method. In addition, these electrode materials can also be used alone or in combination to form a multi-layer structure.

In addition, a thickness of the cathode is 5 to 1000 nm and preferably 10 to 500 nm.

The emission layer may be formed by forming a film of the organic EL dye of the present invention using a physical film formation method such as a vacuum evaporation method or using a chemical film formation method of applying a solution containing the organic EL dye and a binder resin. A thickness of the emission layer is 5 to 300 nm and more preferably 10 to 150 nm.

EXAMPLES

Hereinafter, the present invention will be described by way of examples, but the present invention is not limited to these examples and those skilled in the art can synthesize various organic EL dyes using publicly known methods according to the description of the present invention.

Organic EL dyes used in the present examples were synthesized by the following procedures.

Synthetic Example 1

(Synthesis of Organic EL Dye Containing Anthracene Group for Hole-transporting Group)

(1) Synthesis of Quaternary Anthracene Salt 2

Quaternary anthracene salt 2 was synthesized according to the following scheme 1.

scheme 1

Formula 10

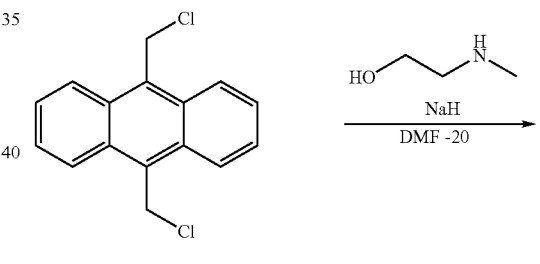

1

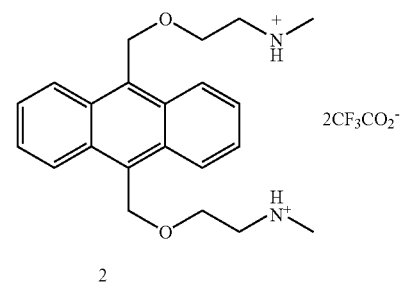

2

That is, 2.06 g (27.0 mmol) of N-methylethanolamine was dissolved in 90 ml of anhydrous DMF in a 200 ml three-necked flask. Then, the resulting solution was cooled to −15° C. and to this, 1.08 g (27 mmol) of a 60% solution of NaH was added over 0.5 hours. After addition, the mixed solution was stirred at −15° C. for 1 hour. Then, 3.00 g (13.5 mmol) of 9,10-bis(chloromethyl)anthracene (1) was added gradually in a crystalline state. The resulting mixture was heated to −10° C. after a lapse of one hour from the completion of this addition and stirred over one night. After the completion of a reaction, DMF was distilled off under a reduced pressure, and the residue was dissolved in 200 ml of methylene chloride and insoluble matter was filtered out. 50 ml of water was added to this, and TFA was added while stirring until the pH of the solution becomes acid. After leaving at rest for 15 minutes, the solution was separated into two layers. A water phase was concentrated by repeating this operation two times and then the water phase was freeze-dried to obtain 2.43 g of quaternary anthracene salt 2 at a yield of 33%.

(2) Synthesis of Light-emitting Group 7

A light-emitting group 7 was synthesized according to the following scheme 2.

scheme 2

Formula 11

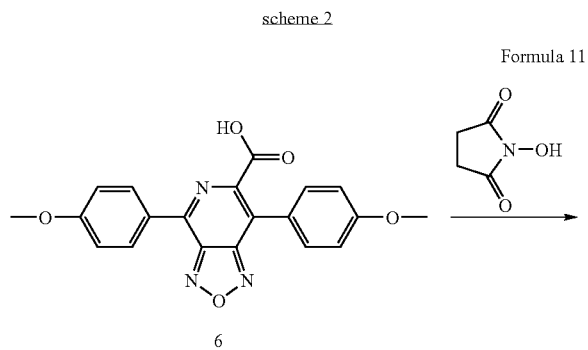

6

1.0 g (0.0026 mol) of oxadiazolopyridinecarboxylic acid and 0.30 g (0.0026 mol) of N-hydroxysuccinimide were dissolved in 20 ml of DMF in a 50 ml three-necked flask. To this, 0.54 g (0.0026 mol) of N,N'-dicyclohexylcarbodiimide was added dropwise over 30 minutes. After adding dropwise, the resulting mixture was stirred at room temperature for 30 hours. Then, DMF was distilled off under a reduced pressure. The residue was isolated and purified by silica gel column chromatography (chloroform) to obtain 0.76 g of active ester 7 of oxadiazolopyridine at a yield of 62%.

(3) Synthesis of Organic EL Dye 8

An organic EL dye 8 was synthesized according to the following scheme 3.

scheme 3

Formula 12

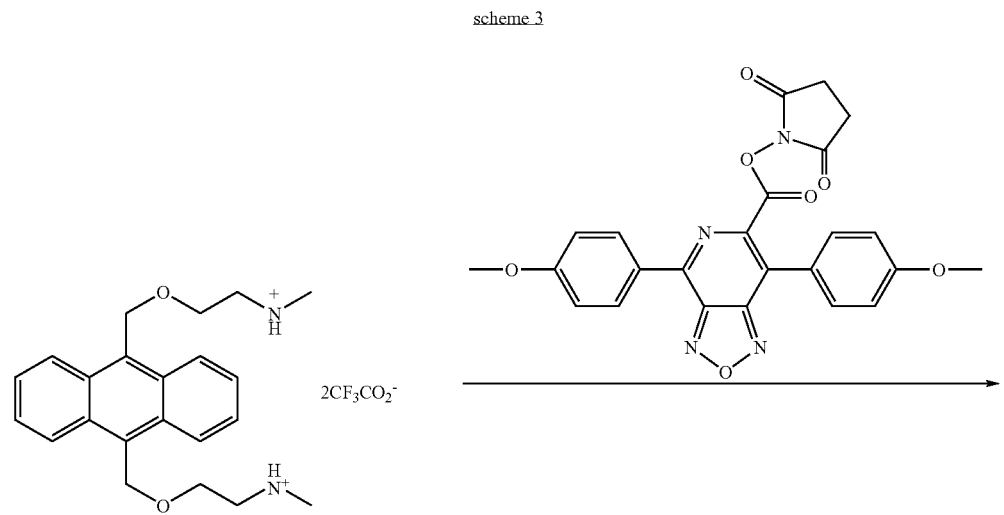

7

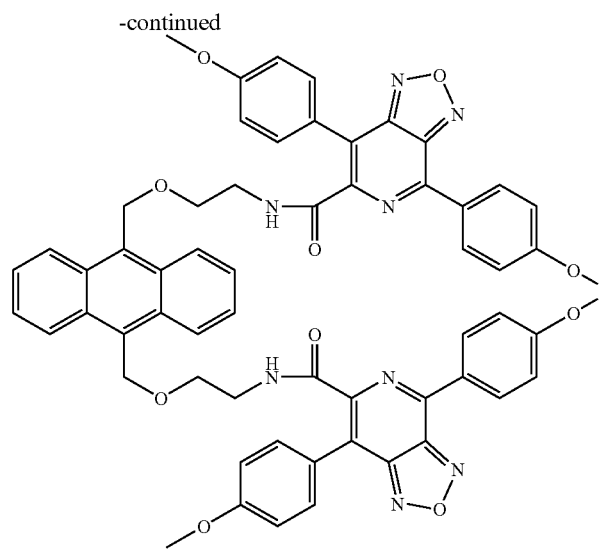

8

That is, 0.35 g (0.26 mmol) of quaternary anthracene salt 2 and 0.22 g (0.57 mmol) of the dye 7 were dissolved in 15 ml of DMF in a 30 ml three-necked flask. To this, 79 μl (2.2 eq.) of triethylamine was added, and the resulting mixture was stirred at room temperature for 3 hours. Then, DMF was distilled off under a reduced pressure. The residue was isolated by silica gel column chromatography (developing solvent; chloroform:methanol=10:2) to obtain 228 mg of the organic EL dye 8 at a yield of 82%.

Synthetic Example 2

(Synthesis of Organic EL Dye Containing Naphthalenediimide Group for Electron-transporting Group)

(1) Synthesis of Quaternary Naphthalenediimide Salt 5

Quaternary naphthalenediimide salt 5 was synthesized according to the following scheme 4.

scheme 4

Formula 13

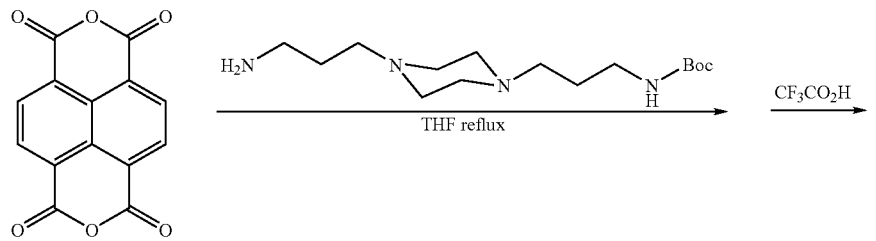

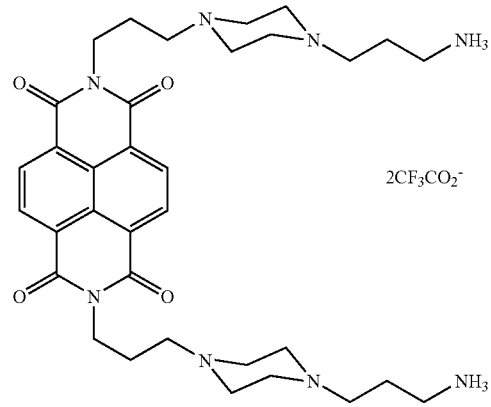

4

That is, 4.6 g (17.3 mmol) of naphthalene-1,4,5,8-tetracarboxylic dianhydride and 12.0 g (39.9 mmol) of 4 were dissolved in 150 ml of anhydrous THF in a 300 ml three-necked flask. Then, the solution was heated and refluxed and stirred for 23 hours. After cooling the solution, 30 ml of chloroform was added to the solution and the mixture was filtered. 200 ml of methanol was added to a filtrate to precipitate a sediment and the sediment was filtered out. The resulting filtrate was concentrated, and the residue was dissolved in methanol and precipitated with water. A sediment was dried to obtain 4.82 g of the quaternary naphthalenediimide salt 5 at a yield of 34%.

(2) Synthesis of Light-Emitting Group 7

As a light-emitting group 7, a light-emitting group synthesized by the method of Synthetic Example 1 was used.

(3) Synthesis of Organic EL Dye 9

An organic EL dye 9 was synthesized according to the following scheme 5.

scheme 5

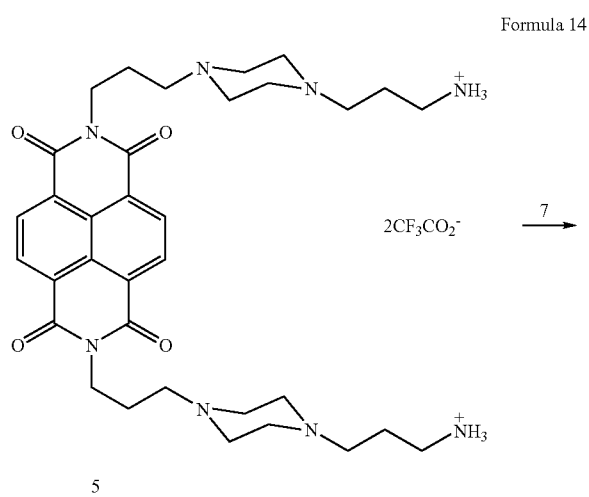

Formula 14

5

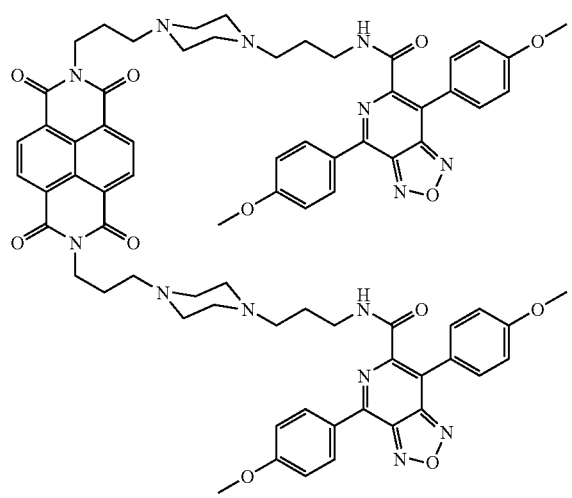

9

That is, 0.16 g (0.26 mmol) of quaternary anthracene salt 2 and 0.22 g (0.57 mmol) of the dye 7 were dissolved in 15 ml of DMF in a 30 ml three-necked flask. To this, 79 µl (2.2 eq.) of triethylamine was added, and the resulting mixture was stirred at room temperature for 3 hours. Then, DMF was distilled off under a reduced pressure. The residue was isolated by silica gel column chromatography (developing solvent; chloroform:methanol=10:2) to obtain 180 mg of the organic EL dye 9 at a yield of 51%.

Example 1

(Preparation of Organic EL Device Having Hole-transporting Group)

A single-layer structure device using ITO for an anode and aluminum for a cathode was prepared by following the following procedure.

Experiment No. 1

20 to 50 mg of an organic EL dye 8 was weighed out and placed on a sublimation panel and then this panel was fixed to an electrode. A glass plate (15 mm×15 mm), on which an ITO electrode was formed, was set in a vapor deposition apparatus ULVAC VPC-260 and a system pressure was reduced to $5 \times 10^{-5}$ torr with a diffusion pump. It took about 3 hours to reach this prescribed pressure. After the system pressure reached $5 \times 10^{-5}$ torr, the organic EL dye was heated by passing a current of 40 to 65 A at 250 V and vapor deposition (a vapor deposition rate was 3 Å/s) was performed until a film thickness of a dye layer reached 30 nm. After the dye layer reached a predetermined vapor deposition film, a power supply was turned off and the system was kept in a state of a reduced pressure for 30 minutes. Then, the reduced pressure of the apparatus was released, aluminum was set at the electrode, and the system pressure was reduced with the diffusion pump. After the system pressure reached $5 \times 10^{-5}$ torr, the aluminum was heated by passing a current of 55 to 75 A at 250 V and vapor deposition (a vapor deposition rate was 20 Å/s) was performed until a film thickness reached 200 nm. After the film thickness reached 120 nm, a power supply was turned off and the vapor deposition apparatus was cooled. After cooling, the reduced pressure of the apparatus was released gradually. The vapor deposition apparatus was opened and a device was taken out. The deposited face of the device was bonded to the mouth of a sample bottle in which a desiccant was previously put with an epoxy adhesive.

Experiments No. 2 and No. 3

Devices of Experiments No. 2 and No. 3 having film thicknesses of a dye layer of 45 nm and 75 nm, respectively, were prepared by the same method as in Experiment 1 using the organic EL dye 8.

(Light Emission Test)

AD-8713 Dual DC POWER SUPPLY manufactured by A & D Co., Ltd. was used as current-generating equipment. A negative terminal was connected to the aluminum electrode and a positive terminal was connected to the ITO electrode of the device. An upper limit current was set at 1.5 A and a voltage was gradually applied with a variable voltage knob, and a light emission test was performed. The results of the test are shown in Table 1. Number of samples for each of Experiments No. 1 to No. 3 was 6 and total 18 samples were prepared. In addition, the values of illuminance were respectively a value measured at an applied voltage of 9 V and an average of six samples.

TABLE 1

| Experimental No. | Thickness of light-emitting film (nm) | Thickness of Al layer (nm) | Starting voltage (V) | Current (A) | Illuminance (cd/cm²) |
|---|---|---|---|---|---|
| 1 | 30 | 200 | 3.6-4.3 | 0.04-0.12 | 1000 |
| 2 | 45 | 200 | 6.5-6.8 | 0.07-0.14 | 1300 |
| 3 | 75 | 200 | 8.3-8.7 | 0.10-0.16 | 1400 |

Figure 7:
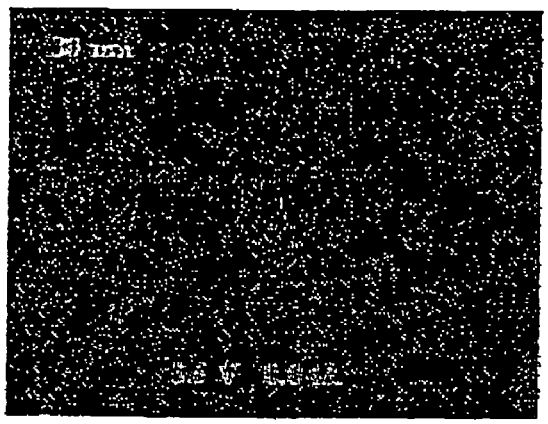
FIG. 7 is a set of photographs showing the results of a light emission test, and photographs (a), (b), (c) and (d) show examples of applied voltages of 3.6 V, 4.5 V, 7.7 V and 9.0 V, respectively.
Figure 7:
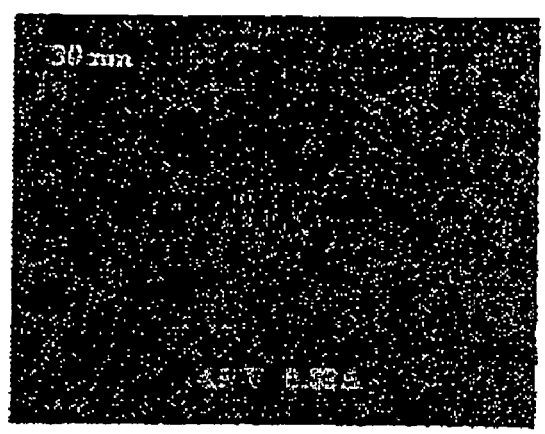
Figure 7:
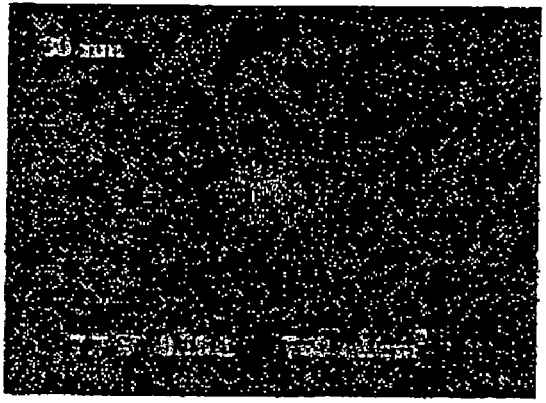
Figure 7:
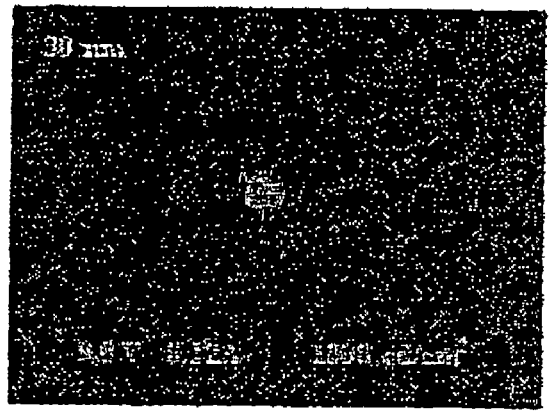

In the light emission test, photographs of the light emission of the device having a film thickness of an emission layer of 30 nm were taken (FIG. 7). In FIG. 7, photographs (a), (b), (c) and (d) show the results of applied voltages of 3.6 V, 4.5 V, 7.7 V and 9.0 V, respectively. The prepared panel started light emission at a low voltage of 3.6 V. It is said that in the organic EL device of a multi-layer structure, devices claimed to have high energy efficiency emit light at about 3V to 5 V. For this situation, the organic EL device of the present invention is the first device of a single-layer structure which can emit light at a low voltage equivalent to or at a lower voltage than that in a device of a multi-layer structure. In addition, its illuminance was improved as the applied voltage was increased.

Example 2

(Preparation of Organic EL Device Having Electron-Transporting Group)

A device of a single-layer structure, having a film thickness of an emission layer of 50 nm, was prepared by the same method as in Example 1 using 50 mg of the organic EL dye 9, and the light emission test was performed. The results of the test are shown in Table 2. A starting voltage was higher than those of Example 1, but yellow-green light was emitted at not more than 10 V. In addition, the value of illuminance was a value measured at an applied voltage of 9 V and an average of six samples.

TABLE 2

| Thickness of light-emitting film (nm) | Thickness of Al layer (nm) | Starting voltage (V) | Current (A) | Illuminance (cd/cm²) |
|---|---|---|---|---|
| 50 | 200 | 9.0-9.7 | 0.05-0.10 | 1000 |

The invention claimed is:

1. An organic EL device comprising an organic layer of a single-layer sandwiched between a pair of electrodes, the organic layer containing an organic EL dye formed by linking a light-emitting group Y represented by the formula: $(Y-L)_n X_m$ to a charge-transporting group X, wherein:
X represents a charge-transporting group, which is a hole-transporting group consisting of a 9,10-bis(chloromethyl)anthracene group,
Y represents a light-emitting group consisting of oxadiazolopyridine derivatives represented by the following formula:

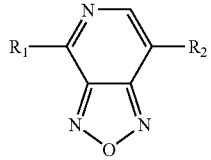

wherein $R_1$ and $R_2$ are independent from each other and represent an aromatic hydrocarbon group optionally having a substituent,
L is a linking group bonding the charge-transporting group and the light-emitting group, and L is represented by the formula $A_1$-$R_1$-$A_2$, wherein $A_1$ is a first bonding group to be bonded to the charge-transporting group and consists of an oxygen atom, $A_2$ is a second bonding group to be bonded to the light-emitting group and consists of an amide group, and $R_1$ is a spacer group linking the first bonding group with the second bonding group and consists of an alkylene group, and m and n are each an integer not less than 1.

2. An organic EL device comprising an organic layer of a single-layer sandwiched between a pair of electrodes, the organic layer containing an organic EL dye formed by linking a light-emitting group Y represented by the formula: $(Y-L)_n X_m$ to a charge-transporting group X, wherein X represents a charge-transporting group, which is an electron-transporting group consisting of a naphthalenediimide group or a phenyldiimide group,
Y represents a light-emitting group consisting of oxadiazolopyridine derivatives represented by the following formula:

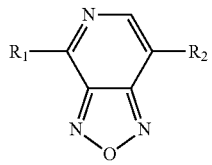

wherein $R_1$ and $R_2$ are independent from each other and represent an aromatic hydrocarbon group optionally having a substituent, and
L is a linking group bonding the charge-transporting group and the light-emitting group, and L is represented by the formula $A_1$-$R_1$-$A_2$, wherein $A_1$ is a first bonding group to be bonded to the charge-transporting group and consists of an N-propylpiperazine group, $A_2$ is a second bonding group to be bonded to the light-emitting group and consists of an amide group, and $R_1$ is a spacer group linking the first bonding group with the second bonding group and consists of an alkylene group, and m and n are each an integer not less than 1.

* * * * *

UNITED STATES PATENT AND TRADEMARK OFFICE
CERTIFICATE OF CORRECTION

PATENT NO. : 8,048,536 B2  
APPLICATION NO. : 10/584313  
DATED : November 1, 2011  
INVENTOR(S) : Shinichiro Isobe Page 1 of 1

It is certified that error appears in the above-identified patent and that said Letters Patent is hereby corrected as shown below:

In paragraph (73), on the front page of the patent,
"Mitsubishi Heavy Industries Ltd., Tokyo (JP)", should be:
--Shinichiro Isobe, Fukuoka (JP) and Mitsubishi Heavy Industries Ltd., Tokyo (JP)--.

Signed and Sealed this
Twenty-eighth Day of February, 2012

David J. Kappos
*Director of the United States Patent and Trademark Office*